(12) United States Patent
Slater et al.

(10) Patent No.: US 6,200,258 B1
(45) Date of Patent: Mar. 13, 2001

(54) RADIOACTIVE THERAPEUTIC SEED HAVING SELECTIVE MARKER CONFIGURATION

(75) Inventors: Charles R. Slater, Fort Lauderdale; Thomas O. Bales; Kevin W. Smith, both of Coral Gables, all of FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/371,243

(22) Filed: Aug. 10, 1999

(51) Int. Cl.$^7$ ........................................................ A61N 5/00
(52) U.S. Cl. ........................................................ 600/8
(58) Field of Search ........................................... 600/1–8

(56) References Cited

U.S. PATENT DOCUMENTS

| | | | |
|---|---|---|---|
| 3,351,049 | 11/1967 | Lawrence | 128/1.2 |
| 4,323,055 | 4/1982 | Kubiatowicz | 128/1.2 |
| 4,702,228 | 10/1987 | Russell, Jr. et al. | 128/1.2 |
| 4,784,116 | 11/1988 | Russell, Jr. et al. | 128/1.2 |
| 4,891,165 | 1/1990 | Suthanthiran | 252/633 |
| 5,011,677 | 4/1991 | Day et al. | 424/1.1 |
| 5,012,357 * | 4/1991 | Schoeppel et al. | 378/65 |
| 5,163,893 | 11/1992 | Suthanthiran | 600/8 |
| 5,342,283 | 8/1994 | Good | 600/8 |
| 5,405,309 | 4/1995 | Carden, Jr. | 600/3 |
| 5,713,828 | 2/1998 | Coniglione | 600/7 |
| 5,728,042 * | 3/1998 | Schwager | 600/3 |
| 5,863,284 * | 1/1999 | Klein | 600/3 |

\* cited by examiner

Primary Examiner—John P. Lacyk
(74) Attorney, Agent, or Firm—David P. Gordon; David S. Jacobson; Thomas A Gallagher

(57) ABSTRACT

Radioactive therapeutic seeds include a carrier structure bearing a radioactive isotope and a radiopaque marker. According to embodiments of the invention, the seeds include a central plug provided with an axial marker and a relatively transverse bore extending through the marker. A second marker may be positioned in the bore, thereby radiographically distinguishing a seed provided with the second marker relative to a seed not provided with the second marker. According to another embodiment of the invention, the isotope is deposited on the outer surface of a hollow radiolucent tube. A biologically-compatible, radiolucent, surface-sealing layer seals the external surface of the tube. A radiopaque marker wire of selected length is positioned in the hollow of the tube. Seeds may be radiographically distinguished from one another by providing seeds with marker wires of different lengths. Each embodiment permits at least two groups of seeds to be radiographically distinguished from one another by the use of differing marker configurations. Each embodiment is further capable of being selectively marked by the physician prior to implantation of the seeds, or by the manufacturer for delivery to the physician in radiographically distinguishable sets. As a result, seeds having different levels of radiation emission can be distinguished in vivo and their effect monitored by the physician.

25 Claims, 4 Drawing Sheets

RADIOACTIVE THERAPEUTIC SEED HAVING SELECTIVE MARKER CONFIGURATION

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of one or more tiny capsules (seeds) into or around a treatment site. The capsules contain a radioactive isotope that irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they are relatively small, typically approximately 0.025 inch in diameter and approximately 0.16 inch long, so that they may be implanted using minimally invasive instruments and techniques. Second, the radioactive isotope must be enclosed in a biocompatible protective package since the seeds are typically not removed and will remain in the body for many years. Third, the isotope should be positioned within the protective package so as to avoid any "hot spots" of radiation. Fourth, each seed preferably includes a radiopaque (e.g. high Z material) marker so that it can be located at the treatment site with the aid of fluoroscopy. Fifth, the protective package and the radiopaque marker are preferably configured such that each does not cast "shadows" in the irradiation pattern of the isotope.

The state of the art of radioactive therapeutic seeds is substantially disclosed in seven U.S. patents: U.S. Pat. No. 5,713,828 to Coiglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent describes many of the essential features of radioactive therapeutic seeds. Lawrence describes radioactive isotopes (I-125, Pd-103, Cs-131, Xe-133, and Yt-169) which emit low energy X-rays and which have relatively short half-lives. Once implanted at a treatment site, these isotopes provide sufficient radiotherapy without posing a radiation danger to the medical practitioner (s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which substantially do not absorb X-rays. The isotope is coated on a rod shaped carrier made of similar X-ray transparent (e.g. low Z) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number material such as gold or tungsten which absorb X-rays.

Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at or around the treatment site.

The Coniglione patent provided a tubular seed adapted for longitudinally receiving suture material to facilitate securing the seed at an implant site. The seed optionally includes a radiopaque band centrally located on the outer surface of the seed, and the radioactive isotope either extends over the entire outer surface of the seed, including over the band, or is coated on the outer surface of the seed from the ends of the seed to areas adjacent the edges of the band.

Despite the fact that radioactive therapeutic seeds have been in use for over thirty years and despite the several significant improvements made in these seeds, many concerns still exist regarding their design. In certain instances where radioactive seed therapy is prescribed for a patient, a physician may desire to have different levels of radioactivity at various locations within the treatment site and thereafter monitor how the tissue is affected by seeds radiating particular levels of radiation. Or the physician may want to implant seeds having isotopes with to different half lives, thereby permitting selected locations to receive radiation over a longer period of time, and monitor which seeds are active. However, according to the known seed designs and methodology, it is not possible to distinguish one seed from another after implantation based upon a seed marker with an imaging systems, e.g., X-ray. Due to the indistinguishability of the seeds, implantation of seeds having different respective properties at a single site of treatment is not purposefully performed.

SUMMARY OF THE INVENTION

It is therefore an object of the invention to provide a system of radioactive therapeutic seeds in which at least one of the therapeutic seeds has a different level of radioactivity relative to other seeds.

It is also an object of the invention to provide a system of radioactive therapeutic seeds in which at least one of the therapeutic seeds has a marker which is different relative to other seeds.

It is another object of the invention to provide radioactive therapeutic seeds in which at least one of the therapeutic seeds has a different level of radioactivity and/or different half-life relative to other seeds and the marker in the at least one therapeutic seed indicates the different level of radioactivity and/or half-life relative to the other seeds.

It is an additional object of the invention to provide radioactive therapeutic seeds in which different seeds are provided with markers of different size which indicate their respective levels of radioactivity or half-life.

It is yet another object of the invention to provide a radioactive therapeutic seed which is adapted to receive markers of various lengths by a physician just prior to insertion.

It is yet a further object of the invention to provide a radioactive therapeutic seed which is adapted to have a marker which can be selectively configured by a physician just prior to insertion.

In accord with these objects which will be discussed in detail below, the radioactive therapeutic seeds of the present invention include a carrier structure bearing a radioactive isotope and a radiopaque marker.

According to a first embodiment of the invention, the isotope bearing structure may be one or more radiolucent particles, preferably made from titanium, aluminum or glass, and preferably spherically shaped. The particles are provided with a thin coating of silver to facilitate the adhesion of the isotope thereto. Also provided is a relatively thick tubular titanium plug having an axial first radiopaque marker therein. The plug preferably includes a circumferential ridge against which the open ends of the two halves of the capsule are butt against and welded thereto. The plug and the marker are provided with a transverse bore accessible from the exterior of the seed. A second marker may be positioned in the bore, thereby radiographically distinguishing a seed provided with the second marker relative to a seed not provided with the second marker; i.e., a seed provided with solely the first marker will have a broken linear radiographic image, while a seed provided with both the first and second markers will have a cross-shaped radiographic image. A plurality of seeds as described may be provided in a system which includes a plurality of seeds and a plurality of second markers for selective insertion into the seeds by a physician. Alternatively, the seeds may be provided to the physician already divided into groups which are distinguishably radiographically marked.

According to a second embodiment of the invention, a seed includes an isotope bearing structure, which is preferably a pair of silver tubes having an interior surface on which the isotope is provided. One silver tube is positioned in each half of the capsule, and the halves of the capsule are welded about a relatively thick centrally located tubular titanium plug. The plug is preferably provided with a first radiopaque marker therein. The plug and the marker are provided with a transverse bore accessible from the exterior of the seed, and the bore may be provided with a second marker, as described above. In addition, the isotope bearing tube is preferably smaller than the interior of each half of the capsule, and a spacer is preferably provided in each half of the capsule between the tube and the plug to prevent relative movement of the tube within the capsule.

According to a third embodiment of the invention, the isotope is deposited on the outer surface of a hollow radiolucent tube. A radiopaque band may be centrally located on the outer surface of the seed, and the radioactive isotope may then either extend over the entire outer surface of the seed, including over the band, or may be coated on the outer surface of the seed from the ends of the seed to areas adjacent the edges of the band. A biologically-compatible, radiolucent, surface-sealing layer seals the external surface of the tube. A radiopaque marker wire is positioned in the hollow of the tube, and where the seed is provided with a radiopaque band, the marker wire is preferably of a length different than the band. It will be appreciated that in a system of seeds according this embodiment, seeds may be radiographically distinguished from one another by providing seeds with marker wires of different lengths.

According to a fourth embodiment of the invention, the seed includes an element on which the isotope is provided, and a marker which can be varied in size or shape by application of energy to the seed.

Each embodiment permits at least two groups of seeds to be radiographically distinguished from one another by the use of differing marker configurations. Each embodiment is further capable of being selectively marked by the physician prior to implantation of the seeds, or by the manufacturer for delivery to the physician in radiographically distinguishable sets. As a result, seeds having different levels of radiation emission can be distinguished in vivo and their effect monitored by the physician.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
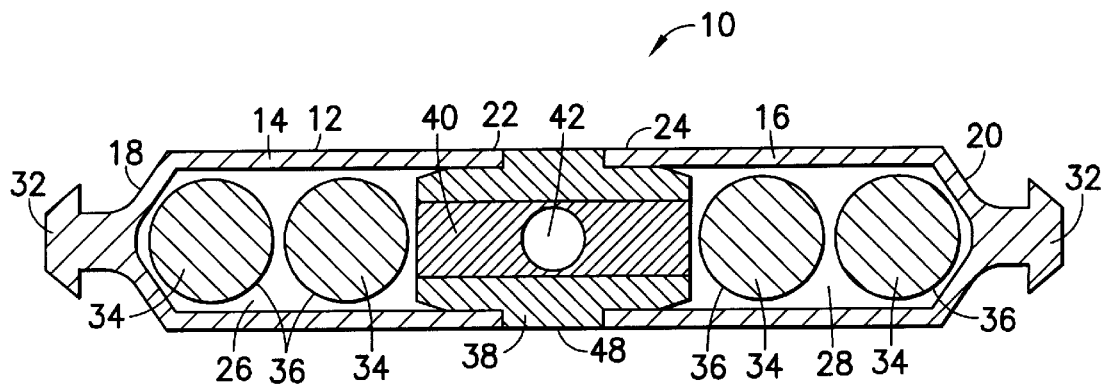
FIG. 1 is an enlarged schematic longitudinal section of a radioactive therapeutic seed according to a first embodiment of the invention.
Figure 2:
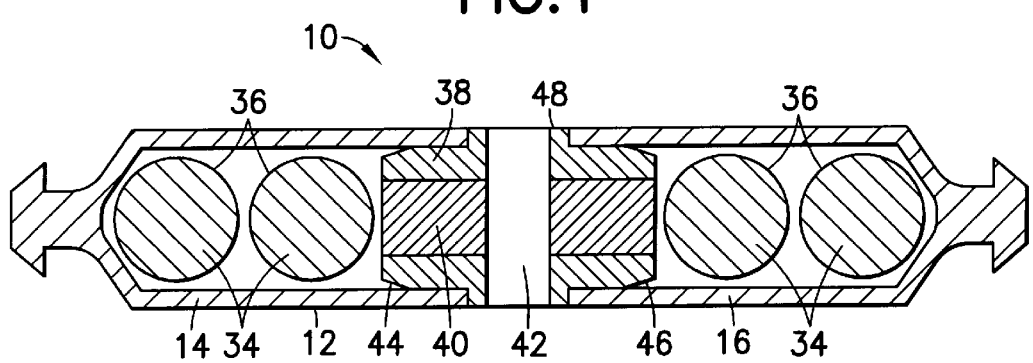
FIG. 2 is a view similar to FIG. 1 with the seed axially rotated by 90° relative to the view shown in FIG. 1.

Referring now to FIGS. 1 and 2, according to a first embodiment of the invention, a radioactive therapeutic seed 10 includes a preferably titanium capsule 12 defined by two halves 14, 16, each having a closed end 18, 20, an open end 22, 24, and an interior portion 26, 28. Each closed end 18, 20 is optionally provided with a connector 32 for connecting to a spacing link (not shown), as described in detail in co-owned U.S. Ser. No. 09/312,215, hereby incorporated by reference herein in its entirety. In the interior portion 26, 28 of each half 14, 16 of the capsule 12, isotope bearing structures 34 are provided. Preferably, the isotope bearing structures 34 are one or more radiolucent particles, preferably made from titanium, aluminum or glass, and preferably spherically shaped. As used herein, the terms "radiotransparent", "radiolucent", "radiotranslucent", and "low Z material" are used interchangeably. The particles 34 are provided with a thin coating of silver over which a radioactive isotope 36 is provided. The two halves 14, 16 of the capsule are welded about a plug 38. The plug 38 is preferably a relatively thick titanium tube. A radiopaque marker 40 is provided axially in the plug 38. Additionally or alternatively, the plug 38 or marker 40 may be comprised of a diamagnetic substance, e.g., a gadolinium metal or salt, to permit visualization of the seed with magnetic resonance imaging (MRI). The plug 38 and preferably the marker 40 are provided with a transverse preferably diametric bore 42 capable of receiving a second radiopaque and/or MRI-visible marker. The plug 38 preferably includes tapered ends 44, 46 to facilitate positioning the open ends 22, 24 thereover, and a central circumferential ridge 48 against which the open ends of the two halves of the capsule are butt against and welded thereto.

Figure 3:
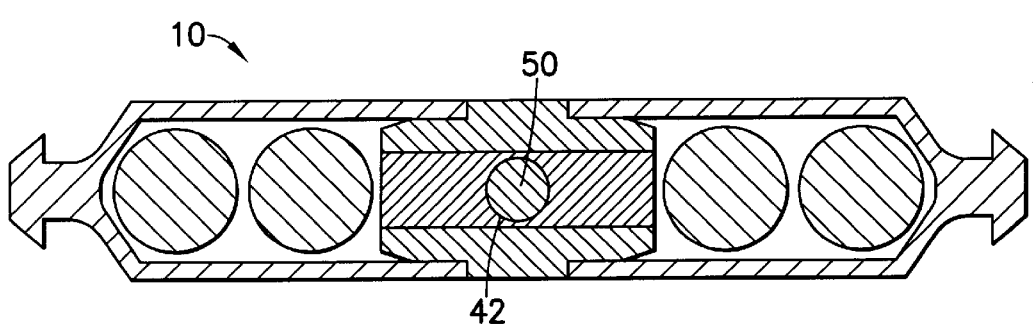
FIG. 3 is a view similar to FIG. 1 with the radioactive therapeutic seed according to a first embodiment of the invention shown with a secondary marker provided therein.
Figure 4:
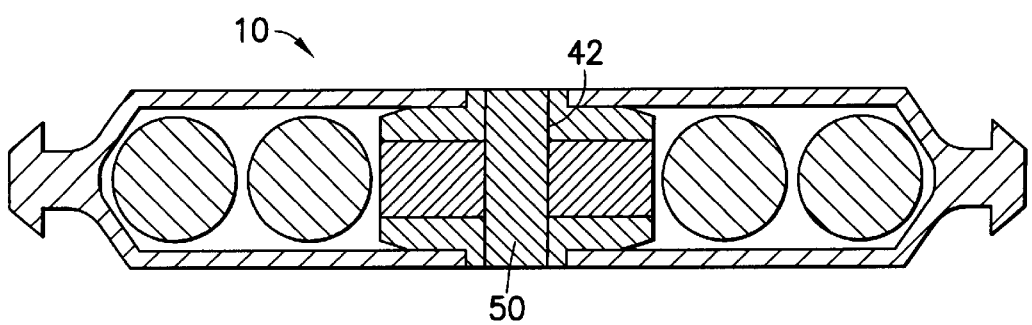
FIG. 4 is a view similar to FIG. 3 with the seed axially rotated by 90° relative to the view shown in FIG. 3.

Turning now to FIGS. 3 and 4, a second radiopaque marker 50 may be positioned in the bore 42 of the seed 10, thereby radiographically distinguishing a seed provided with the second marker relative to a seed not provided with the second marker; that is, a seed provided with solely the first marker 40 will have in one orientation a broken linear radiographic image (FIG. 2), while a seed provided with both the first marker 40 and second marker 50 will have in one orientation a cross-shaped radiographic image (FIG. 4). A system may thereby be provided which includes a plurality of seeds 10 and a plurality of second markers 50 for selective insertion into the seeds by a physician prior to implantation of the seeds into a patient. Alternatively, the seeds may be provided to the physician already divided into groups which are distinguishably radiographically marked; i.e., provided with and without second markers.

Figure 5:
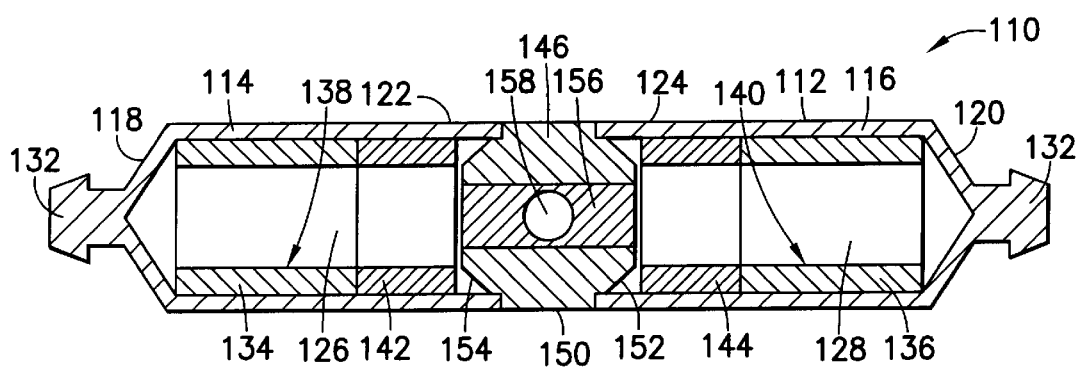
FIG. 5 is an enlarged schematic longitudinal section of a radioactive therapeutic seed according to a second embodiment of the invention.
Figure 6:
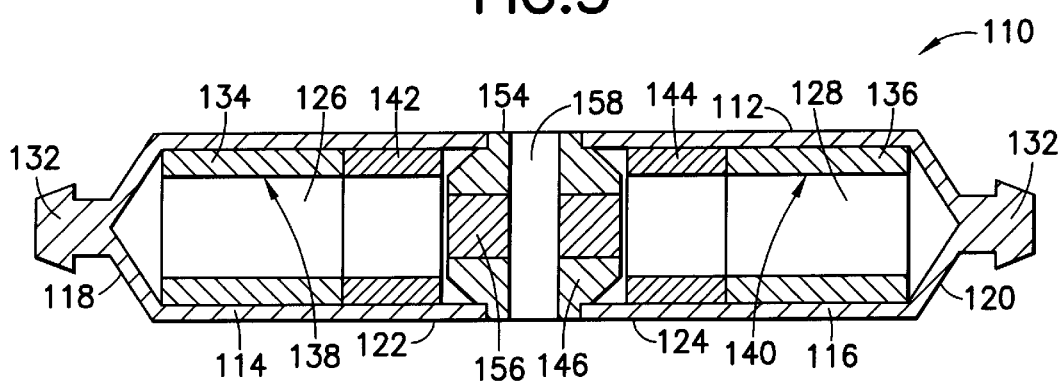
FIG. 6 is a view similar to FIG. 5 shown with the seed axially rotated by 90° relative to the view shown in FIG. 5.
Figure 7:
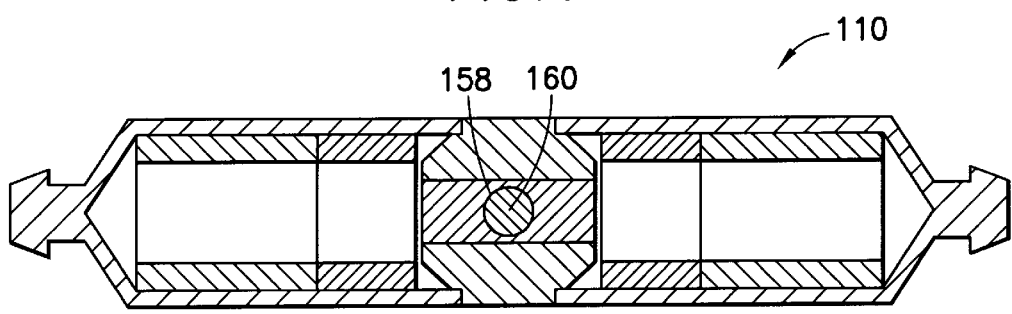
FIG. 7 is a view similar to FIG. 5 with the radioactive therapeutic seed according to a first embodiment of the invention shown with a secondary marker provided therein.
Figure 8:
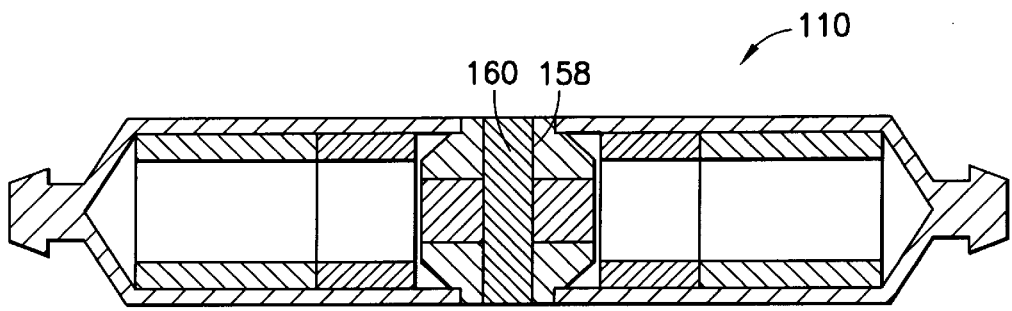
FIG. 8 is a view similar to FIG. 7 shown with the seed axially rotated by 90° relative to the view shown in FIG. 7.

Referring now to FIGS. 5 and 6, a second embodiment of a therapeutic seed 110 according to the invention is shown. The seed 110 includes a radiolucent titanium capsule 112 defined by two halves 114, 116, each having a closed end 118, 120, optionally provided with a connector 132, an open end 122, 124, and an interior portion 126, 128. In the interior portion 126, 128 of each half 114, 116 of the capsule 112, a silver tube 134, 136 is provided. Each tube 134, 136 is preferably 0.025 inch in length and preferably has a wall thickness of 0.004 inch. The interior surfaces 138, 140 of the tubes are coated with I-125 or another radioisotope. As the tubes 134, 136 may be shorter than the length of the interior portion 126, 128, spacers 142, 144 may be provided in the interior portion to prevent relative movement of the tubes within the capsule 112. The two halves 114, 116 of the capsule are welded about a plug 146. The plug 146 is preferably a titanium tube having tapered ends 150, 152 to facilitate positioning the open ends 122, 124 thereover, and a central circumferential ridge 154 against which the open ends of the two halves of the capsule are butt against and welded thereto. A radiopaque marker 156 is provided in the plug 146. Additionally or alternatively, the marker 156 may be MRI-visible. The plug 146 and the marker 156 are provided with a diametric bore 158 accessible from the exterior of the seed 110. Turning now to FIGS. 7 and 8, the bore 158 may be provided with a second marker 160, as described above, to thereby radiographically distinguish seeds provided with and without second markers.

Figure 9:
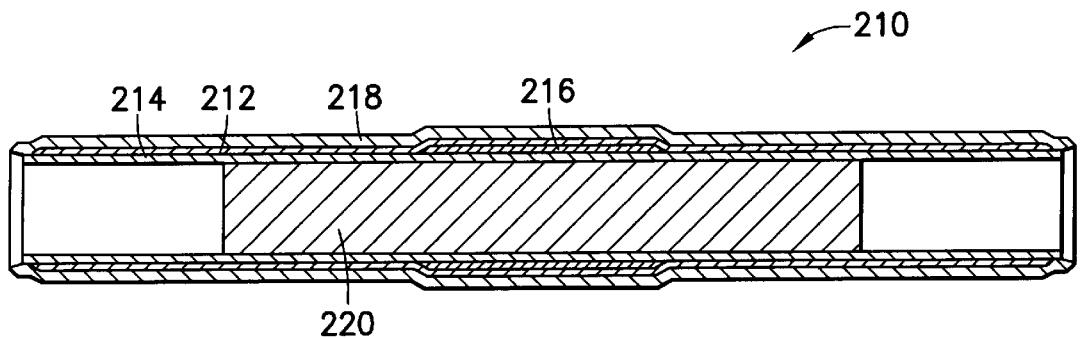
FIG. 9 is an enlarged schematic longitudinal section of a radioactive therapeutic seed according to a third embodiment of the invention shown with a wire marker having a first length.
Figure 10:
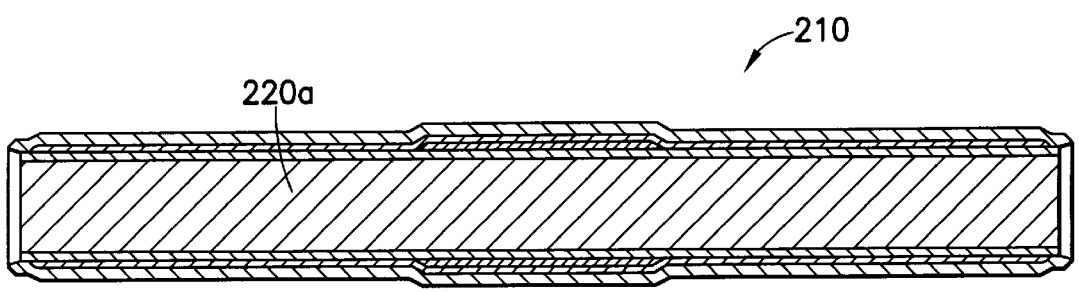
FIG. 10 is a view similar to FIG. 9 shown with a wire marker having a second length different than the first length.

Referring now to FIG. 9, a third embodiment of a radioactive therapeutic seed according to the invention is shown. The seed 210 comprises a radioactive isotope 212 deposited on the outer surface of a hollow radiolucent tube 214. Optionally, a radiopaque band 216 may be centrally located on the outer surface of the tube 214, and the radioactive isotope 212 may then either extend over the entire outer surface of the tube 214, including over the band 216, or may be coated on the outer surface of the seed from the ends of the seed to areas adjacent the edges of the band. A biologically-compatible, radiolucent, surface-sealing layer 218 seals the external surface of the tube 214. The seed as described thus far is substantially similar to that disclosed in U.S. Pat. No. 5,713,828 which is hereby incorporated by reference herein in its entirety. In accord with the invention, a radiopaque marker wire 220 is positioned in the hollow of the tube 214, and where the seed is provided with a radiopaque band 216, the marker wire is preferably of a length different than the band. The length of the marker wire 220 may be selected to provide an indication of the level of radioactivity of the seed 210. For example, referring to FIG. 10, a marker wire 220a relatively longer than marker wire 220 shown in FIG. 9 may be used to radiographically distinguish the seed shown in FIG. 9 from the seed shown in FIG. 10. It will be appreciated that, in accord with this embodiment, a system of seeds may be provided which includes at least two sets of seeds radiographically distinguishable from each other.

Figure 11:
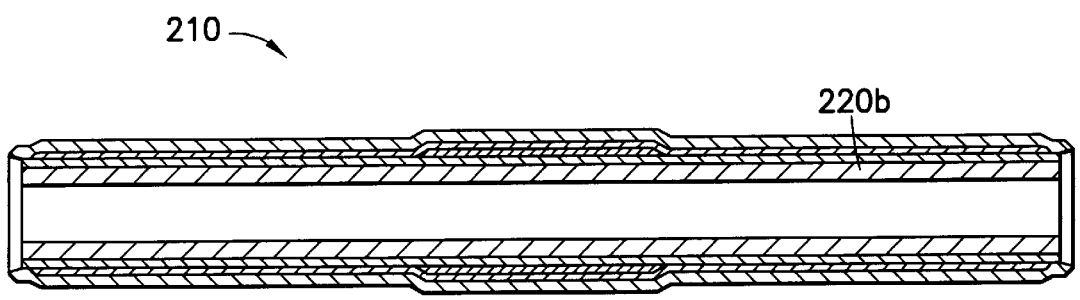
FIG. 11 is a view similar to FIG. 9 shown with two tubular co-axial markers.

With respect to the third embodiment, it will be appreciated that the marker wire may alternatively be a tubular marker 220b, thereby permitting the passage of a suture wire therethrough to couple the seed to the tissue at an implant site (FIG. 11). It will be further appreciated that multiple markers may be provided in the hollow of the tube, e.g., a tubular marker and a marker wire extending through the tubular marker. Additionally, transverse or diametric holes may be provided in the tube, and the marker wire may be positioned within with holes; i.e., the orientation of the second markers in the first and second embodiments. Furthermore, radiolucent plugs may be provided on either end of the marker wire or tubular marker to seal the seed about the markers.

Figure 12:
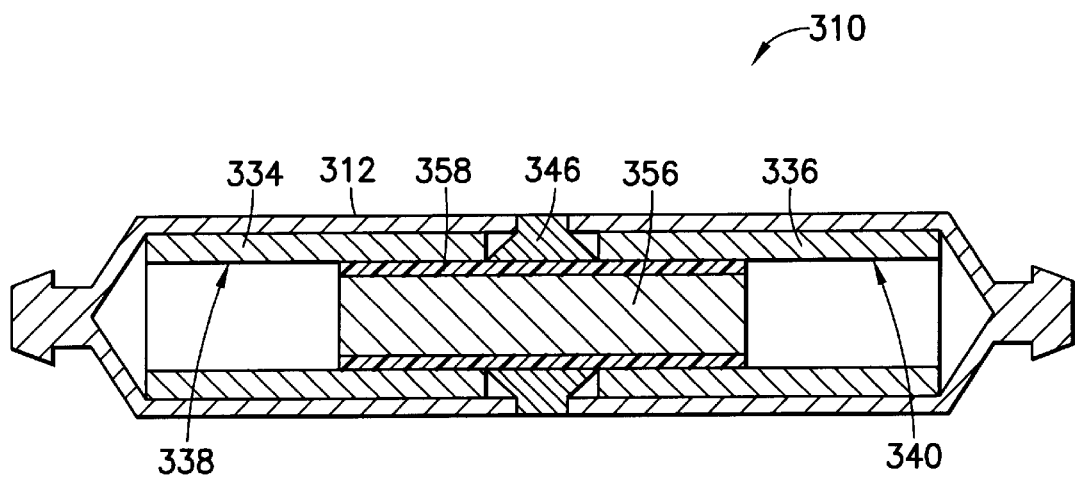
FIG. 12 is an enlarged schematic longitudinal section of a radioactive therapeutic seed according to a fourth embodiment of the invention shown with a marker having a first shape.
Figure 13:
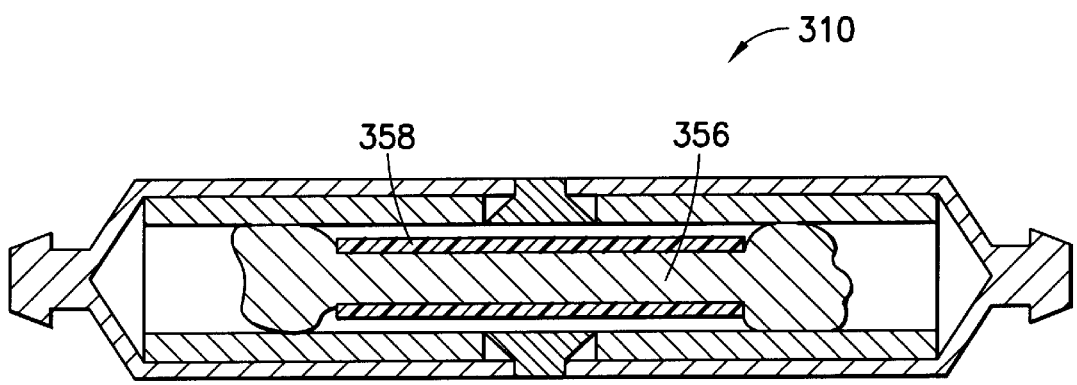
FIG. 13 is a view similar to FIG. 12 with the marker having a second shape.

Turning now to FIG. 12, a fourth embodiment of a therapeutic seed 310 according to the invention is shown. The seed 310, substantially as described with respect to the second embodiment, includes a radiolucent titanium capsule 312 welded about a plug 346, and one or more tubes 334, 336 within the capsule having I-125 or another radioisotope coated on the interior surfaces 338, 340 of the tubes. A radiopaque marker 356 is provided within the capsule. According to the fourth embodiment, the marker is a radiopaque material having a low melting point, e.g., an indium alloy, a bismuth alloy, or a solder or other eutectic, which is in solid form when the seed 310 is at body temperature. A heat-shrinkable or elastic sleeve 358 may be provided over the marker. Referring to FIG. 13, when heat is applied to the seed 310, such that the seed is at a temperature greater than body temperature, the radiopaque material of the marker 356 melts and the sleeve 358 shrinks about the melted material, forcing at least some of the radiopaque material from the sleeve such that the marker 356 changes shape, e.g., forms a relatively longer bar-bell shape.

It will be appreciated that in the fourth embodiment, otherwise like seeds which were made at different times, and therefore have different remaining useful life through which they may provide a therapeutic dose of radiation, may be separately identified and used together. For example, heat may be applied to a first set of relatively older seeds to cause their markers to be relatively longer than a second set of relatively newer seeds. Once implanted, the position of the seeds may be individually monitored by distinguishing their respective markers.

Each embodiment permits at least two groups of seeds to be radiographically distinguished from one another by the use of differing marker configurations. Each embodiment is further capable of being selectively configured by the physician prior to implantation of the seeds, or by the manufacturer for delivery to the physician in radiographically distinguishable sets. As a result, seeds having different levels of radiation emission can be distinguished in vivo and their effect monitored by the physician. This is particularly useful in that the invention permits discrete monitoring of two or more sets of seeds, e.g., seeds having relatively different levels of radiation, seeds having relatively different radiation distribution, or seeds having radioactive isotopes with relatively different half-lives, as each set may be radiographically distinct. In addition, it will be appreciated that the provision of a second marker to each embodiment does not detrimentally affect the relatively isotropic distribution of the seeds.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciated that certain features of one embodiment may be combined with features of another embodiment to provide yet additional embodiments. It will be appreciated that numerous other seed designs may be configured to receive a secondary marker to thereby permit relative seed differentiation, and that the particular designs disclosed herein are only exemplary. In addition, while the second marker, in the first and second embodiments, or the marker wire, in the third embodiment, have been described as being radiopaque, it will be appreciated that such markers may be MRI-visible. Likewise, while the first marker or marker band has been described as being radiopaque, each may be MRI-visible, and the second marker and marker wire may be radiopaque. Also, while the second marker in the first and second embodiments has been described as preferably being diametrically and/or transversely oriented, it will be appreciated that the second marker need only be angled relative to the first marker or non-axial relative to the longitudinal axis of the capsule. In addition, the wire marker in the third embodiment may be cylindrical or an elongate rectangular shape, each being substantially a wire at the scale of brachytherapy seeds. Furthermore, while each capsule is preferably formed from two halves (for purposes of isotropic radiation distribution), it will be appreciated that the two parts forming the capsule need not be halves, e.g., one part being one third the length of the capsule and the other part begin two thirds the length of the capsule. Moreover, while the isotope bearing surface has been disclosed as the outer surface in particular embodiments and the inner surface in other embodiments, it will be appreciated that either of the inner and outer surfaces may be used as the isotope bearing surface, though it is believed that the embodiments as described provide the most isotropic radiation distribution. In addition, while a particular seed has been disclosed having a marker which changes shape when energy is applied to the seed, it will be appreciated that such markers may be used in seeds having different radioisotope bearing elements and different capsule configurations. Also while a meltable marker has been described having a heat shrinkable or elastic sleeve thereabout, it will be appreciated that the sleeve is not required, and that the marker can be altered from a defined shape, e.g., cylindrical, to an amorphous configuration upon melting. Further, where a sleeve is used, it will be appreciated that the marker after heating, if substantially melted, may take the configuration of two or more separated masses. It will therefore be appreciated by those skilled in the art that yet other modifications could be made to the provided invention without deviating from its spirit and scope as claimed.

What is claimed is:

1. A radioactive therapeutic seed, comprising:
   a) a radiolucent capsule having a longitudinal axis;
   b) a carrier structure carrying a radioactive isotope provided in said capsule; and
   c) a first marker substantially within said capsule which permits at least one of a radiographic and a MRI image of said first marker, said first marker having an opening non-axial with said longitudinal axis of said capsule.

2. A radioactive therapeutic seed according to claim 1, wherein:
   said first marker is radiopaque.

3. A radioactive therapeutic seed according to claim 1, further comprising:
   d) a second marker provided in said opening in said first marker which permits at least one of a radiographic and a MRI image of said second marker,
   wherein a seed provided with said first and second markers has at least one of a radiographic and a MRI image which is distinguishable from a seed provided without said second marker.

4. A radioactive therapeutic seed, comprising:
   a) a radiolucent capsule having a longitudinal axis;
   b) a carrier structure carrying a radioactive isotope provided in said capsule;
   c) a first marker which permits at least one of radiographic and MRI visualization of said first marker; and
   d) a second marker substantially completely within said first marker which permits at least one of radiographic and MRI visualization of said second marker.

5. A radioactive therapeutic seed, comprising:
   a) a tube having a longitudinal hollow;
   b) a radiopaque band provided about said tube;
   c) a radioactive isotope provided on said tube; and
   d) a marker extending at least partially within said hollow, said marker permitting at least one of a radiographic and a MRI image of said marker.

6. A radioactive therapeutic seed according to claim 5, wherein:
   said marker is a wire.

7. A radioactive therapeutic seed according to claim 5, wherein:
   said marker is a tube.

8. A radioactive therapeutic seed system according to claim 5, further comprising:
   e) a sealing layer extending over said radioactive isotope.

9. A radioactive therapeutic seed system, comprising:
   a) a first radioactive therapeutic seed having a first carrier structure provided with a first isotope which emits a first level of radiation and a first marker which is viewable as a first image in at least one of a radiographic and a MRI image, said first image having a first configuration; and b) a second radioactive therapeutic seed having a second carrier structure provided with a second isotope which emits a second level of radiation and a second marker which is viewable as a second image in at least one of a radiographic and a MRI image, said second image having a second configuration different than said first configuration.

10. A radioactive therapeutic seed system according to claim 9, wherein:

said second level of radiation is different than said first level of radiation.

11. A radioactive therapeutic seed system according to claim 9, wherein:

said first configuration is a linear configuration and said second configuration is a cross-shaped configuration.

12. A radioactive therapeutic seed system according to claim 9, wherein:

said first marker is a band and said second marker includes a band component and another component.

13. A radioactive therapeutic seed system according to claim 12, wherein:

said other component is a tube.

14. A radioactive therapeutic seed system according to claim 12, wherein:

said other component is a wire.

15. A radioactive therapeutic seed system according to claim 9, wherein:

said first marker is one of a wire and a tube having a first length and said second marker is one of a wire and a tube having a second length different that said first length.

16. A radioactive therapeutic seed system according to claim 9, wherein:

said first isotope has a first half-life, and said second isotope has a second half-life different than said first half-life.

17. A radioactive therapeutic seed, comprising:

a) a radiolucent capsule;

b) a carrier structure carrying a radioactive isotope provided in said capsule;

c) a marker which permits at least one of radiographic and MRI visualization of said seed, said marker adapted to change configuration upon an application of energy to said seed.

18. A radioactive therapeutic seed according to claim 17, wherein:

said marker is a eutectic substance.

19. A radioactive therapeutic seed according to claim 17, wherein:

said marker is covered in a sleeve which is at least one of elastic and heat shrinkable.

20. A radioactive therapeutic seed, comprising:

a) a radiolucent capsule having a longitudinal axis;

b) a carrier structure carrying a radioactive isotope provided in said capsule; and c) a MRI-visible first marker having an opening non-axial with said longitudinal axis of said capsule.

21. A radioactive therapeutic seed, comprising:

a) a radiolucent capsule having a longitudinal axis;

b) a carrier structure carrying a radioactive isotope provided in said capsule; and c) a first marker positioned axially within said capsule and which permits at least one of a radiographic and a MRI image of said first marker, said first marker having a substantially diametric opening.

22. A radioactive therapeutic seed, comprising:

a) a radiolucent capsule having a longitudinal axis;

b) a carrier structure carrying a radioactive isotope provided in said capsule;

c) a first marker which permits at least one of a radiographic and a MRI image of said first marker, said first marker having an opening non-axial with said longitudinal axis of said capsule; and d) a second marker which permits at least one of a radiographic and a MRI image of said second marker, said second marker oriented non-parallel relative to said first marker and extending through said opening in said first marker.

23. A radioactive therapeutic seed according to claim 22, wherein:

said second marker is oriented substantially transverse said first marker.

24. A radioactive therapeutic seed, comprising:

a) a radiolucent capsule having a longitudinal axis;

b) a carrier structure carrying a radioactive isotope provided in said capsule; and c) a first marker which permits at least one of a radiographic and a MRI image of said first marker, said first marker having an opening non-axial with said longitudinal axis of said capsule, said first marker being located nearer a center of said capsule than said radioactive isotope.

25. A radioactive therapeutic seed, comprising:

a) a radiolucent capsule having a longitudinal axis;

b) a carrier structure carrying a radioactive isotope provided in said capsule;

c) a first marker which permits at least one of a radiographic and a MRI image of said first marker, said first marker having an opening, said first marker being located nearer said longitudinal axis of said capsule than said radioactive isotope; and d) a second marker extending through said opening in said first marker.

* * * * *